United States Patent [19]

Harvill

[11] 3,955,402

[45] May 11, 1976

[54] PASS LEVEL TESTER FOR GLASS BOTTLES

[75] Inventor: William Andrew Harvill, Decatur, Ga.

[73] Assignee: The Coca-Cola Co., Atlanta, Ga.

[22] Filed: Sept. 22, 1975

[21] Appl. No.: 615,432

[52] U.S. Cl. ................................................. 73/37
[51] Int. Cl.² ........................................... G01M 3/02
[58] Field of Search ............ 73/37, 49.2, 49.3, 49.4, 73/52, 49.5

[56] References Cited
UNITED STATES PATENTS

| | | | |
|---|---|---|---|
| 3,771,649 | 11/1973 | Strauss | 73/37 |
| 3,785,195 | 1/1974 | Yasuhiro | 73/37 |
| 3,805,594 | 4/1974 | Hayashi | 73/37 |

Primary Examiner—Donald O. Woodiel
Attorney, Agent, or Firm—W. Dexter Brooks

[57] ABSTRACT

An apparatus for testing the internal pressure strength of glass bottles is described. The system utilizes water as a pressure test medium which is introduced into the test bottles and pressurized to predetermined pressure levels in stepped increments. Pressurization of the water is effected by a gas driven piston in the water supply line. A plurality of pressure control switches in the water supply line step the water pressure through said predetermined levels. A control circuit is provided for sequentially actuating said pressure switches for predetermined durations. Indicator means are provided on a control panel to indicate the test pressure level under which the test apparatus is operating at any given time, (i.e., guage), as well as the test pressure levels passed (i.e., lamps).

11 Claims, 7 Drawing Figures

PASS LEVEL TESTER FOR GLASS BOTTLES

BACKGROUND OF THE INVENTION

1. Field of Invention

The present invention relates to a system and apparatus for hydrostatically testing the internal pressure strength of glass bottles at predetermined pass levels controlled by an automatic sequencer.

2. Description of Prior Art

Heretofore apparatus for hydrostatically testing the internal pressure of glass bottles have existed. However, there are a number of drawbacks to the use of these prior art testers, particularly in the realm of economics and practicality.

For example, in those prior art testers which were not fully automated, constant supervision and adjustments were required by a skilled test operator in order to make a plurality of pressure tests on a given bottle or container. This necessitated that the operator make manual adjustments by the use of pressure gauges and control valves to obtain each of a plurality of desired water pressure levels. This method of operation proved to be very time consuming and subject to certain inaccuracies depending on the skill of the operator.

Because of the foregoing problems, the industry in the last decade has directed its efforts towards the development of fully automated test apparatii. However, these presently available automated test apparatii also suffer a drawback in the industry since they subject glass bottles to an infinite number of pressure levels, which is undesirable and impractical in that segment of the industry which uses a test apparatus quality control program to inspect glass containers at predetermined pass levels. Moreover, these automated versions are bulky, expensive and sophisticated insofar as their pressure-producing elements and the control circuitry therefor. Accordingly, there has arisen a need in the industry for a reliable automated test apparatus, preferably of simple construction for hydrostatically testing the internal pressure strength of glass bottles at predetermined pass levels controlled by an automatic sequencer.

SUMMARY OF THE INVENTION

It is, accordingly, an object of the present invention to provide a system for automatically testing the internal pressure strength of glass containers at predetermined pressure pass levels controlled by an automatic sequencer.

It is another object of the present invention to provide an apparatus for supporting the container under test throughout the test sequence in an enclosed protective housing.

It is further an object of the present invention to provide means for indicating the existing water pressure levels at any given time within the test sequence.

It is further an object of the present invention to provide means for indicating the test pressure levels passed at any given time within the test sequence.

It is still a further object of the present invention to provide an apparatus for testing internal pressure levels of glass bottles which rapidly and accurately sequences the test pressure levels through predetermined values in stepped increments.

These and other objects of the present invention are fulfilled by providing a water system for supplying water to the bottle under test; a gas system for pressurizing the water; a control system for automatically sequencing the water pressure to predetermined levels in steps or increments; and an apparatus for supporting and housing all system components and the glass containers under test.

The use of water as a pressure test medium is desirable for both safety and accuracy purposes since water does not expand or explode when a bottle breaks during the testing operation. Also, the use of water as the test medium allows pressure to be applied more rapidly than the use of other pressure test media, such as air (i.e., pneumatically). Insofar as accuracy considerations, the rate of the initial ramp time of pressure in the test bottle is increased by the use of water, as opposed to the use of gas or other test medium, which is hereinafter explained in more detail in relation to "equivalent pressures". Moreover, the use of water further enhances the accuracy of the test apparatus since its lower expansion characteristics maintain a more constant test pressure level in the glass bottles under test, than would otherwise occur if another pressure test medium, such as gas, were to be used.

A pressure chamber is provided which communicates with both the water system and gas system of the present invention. A piston is disposed within the pressure chamber and defines an interface between the water and gas in the chamber. Therefore, the water pressure in the bottle can be controlled within predetermined limits by the gas pressure generated by the gas system in the pressure chamber which drives the piston.

The water system also includes in the water supply line to the bottle or container under test a plurality of pressure control switches. The actuation of a selected one of said switches effects a predetermined water pressure level in the test bottle. In the present invention automatic sequencing means are provided to actuate the perspective pressure switches to step the test pressure levels in increments from a first level controlled by a first pressure switch to progressively higher levels controlled by each of the remaining switches. Indicating means are provided to inform the operator at any given instant which test pressure level has been reached. Accordingly, if a bottle should burst, the test pressure level causing the same can be determined by visual inspection of a series of panel lamps of the indicating means. Also, the indicating means embody a panel gauge to verify proper operation of the test apparatus.

Therefore, the test performed by the pressure tester of the present invention can be programmed in advance, greatly reducing the skills required by an operator who performs the test, and greatly reducing the time required to make a plurality of tests at selected discrete pressure levels.

The pressure levels referred to throughout the description of the present invention are equivalent pressures, i.e., a pressure which exists in the test bottle for a predetermined duration. This is necessary since glass bottle strength is a function of not only pressure, but duration of pressure and time. Accordingly, the automatic sequencing timer of the present invention holds each stepped pressure level at said level for predetermined periods of time. Since equivalent pressure is a function of both pressure and duration, the value thereof can be controlled by varying either the actual pressure applied to the test bottle and/or the time thereof. Thus, in the system of the present invention the equivalent pressure levels of the stepped increments can be adjusted in either duration or pressure magnitude to achieve the equivalent pressure desired.

In a preferred embodiment of the present invention a four second time duration for each pressure level is used to reduce overall test time. Since equivalent pressure is based on a one minute test duration, it is necessary to be able to convert between actual pressure and equivalent pressure for different time durations T. This may be done by the following formula which is derived from *Journal of Applied Physics*, Volume 17, March 1946, pages 189–195, "The Fatigue Modulus of Glass", by J. L. Glathart and F. W. Preston:

Equivalent Pressure = Actual Pressure $(A + B \log_{10} T)$

For example, if $A = 0.75$ and $B = 0.14$, then for an equivalent pressure of 150 p.s.i. and a time duration T of 4 seconds, actual pressure can be calculated to be 180 p.s.i. Therefore, the application of 180 p.s.i. for 4 seconds is equivalent to the application of 150 p.s.i. for 1 minute.

The initial ramp time of the pressure in the test bottle is an important feature of the present invention since it avoids fatigue of the test container, which fatigue, if it were to occur, would cause the strength of the test container to be reduced and breakage to occur at an equivalent pressure level less than the actual equivalent pressure level of the test container.

The mechanical apparatus of the present invention includes a test chamber for safely housing the bottle under test and means for supporting all control components in a compact substantially portable assembly.

BRIEF DESCRIPTION OF THE DRAWINGS

The objects of the present invention and the attendant advantages thereof will become more readily apparent with reference to the accompanying drawings wherein.

DESCRIPTION OF PREFERRED EMBODIMENTS

Figure 1:
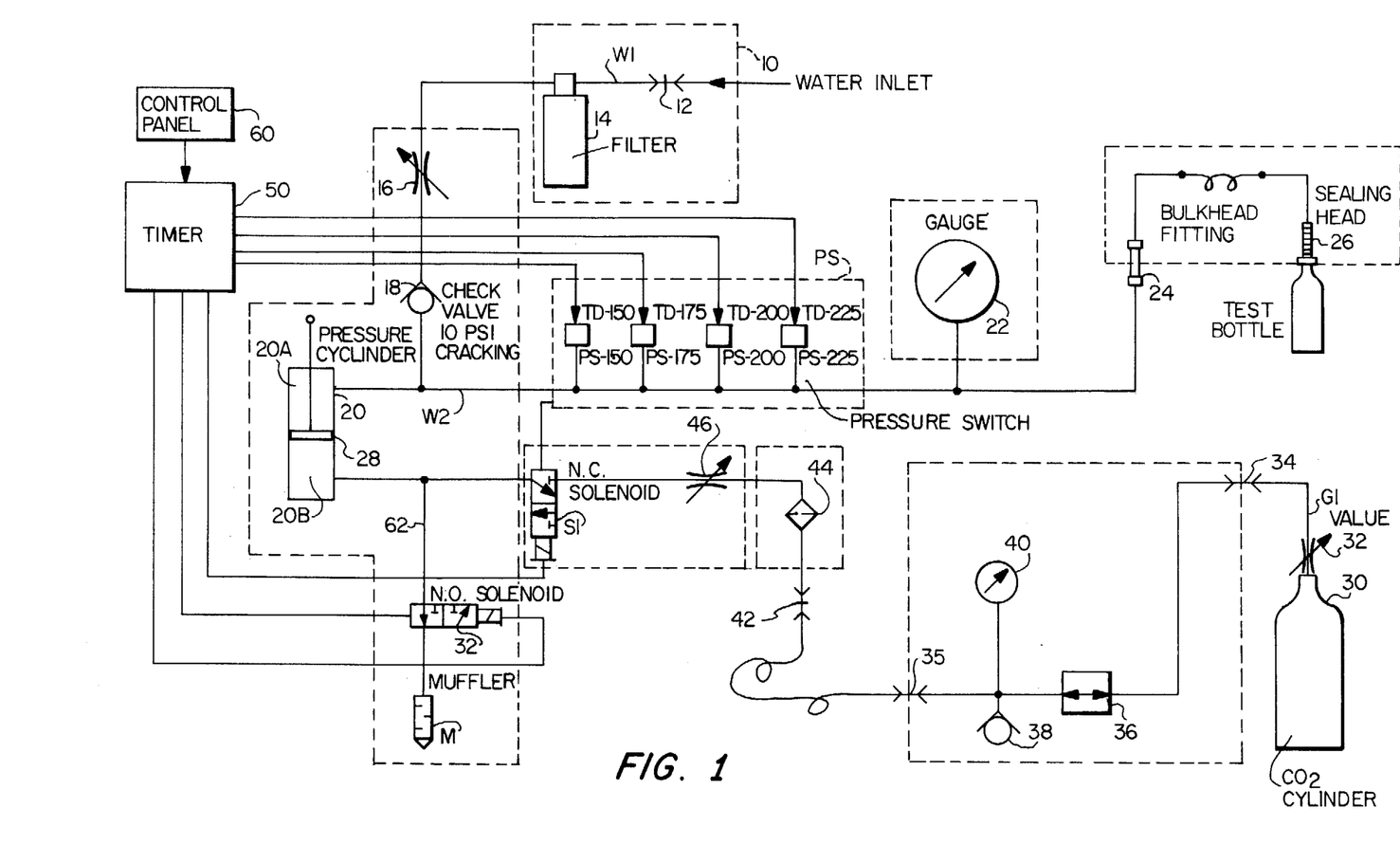
FIG. 1 is a diagrammatic view illustrating the pass level testing system of the present invention.

Referring in detail to the drawings there is illustrated in FIG. 1 a flow diagram of the test system of the present invention.

A test bottle TB is coupled to water supply or inlet 10 via water supply lines W1, W2.

Water supply line W1 includes a quick connector 12 coupled to inlet 10, a filter 14, a needle valve 16, and a check valve 18. Filter 14 is provided to reduce incoming contaminates from the water supply and needle valve 16 provides an adjustment means for reducing the incoming (city) water pressure.

Line W1 is coupled to line W2 which extends from pressure chamber of cylinder 20 to test bottle TB. Pressure cylinder 20 includes a piston 28 movably disposed therein which separates the piston into chambers 20A, 20B. Chamber 20A communicates with water supply line W2 while chamber 20B communicates with gas supply line G1 to be more fully described hereinafter.

Disposed within line W2 is pressure switch control means PS which includes a plurality of selectively operable switches PS-150, PS-175, PS-200, PS-225. Switches PS permit the pressure in line W2 and thus in bottle TB to build up to discrete and predetermined levels in response to command signals from timer 50 to be described hereinafter. For example, if switch PS-150 is enabled by timer 50, the pressure in line W2 rises to 150 p.s.i. and remains at that level for a duration determined by the command signal from timer 50. The application of command signals to any of the other switches PS-175, PS-200, PS-225 will regulate the line pressure of W2 to 175 p.s.i., 200 p.s.i., and 225 p.s.i., respectively, in a similar manner.

Pressure switches PS are in the nature of pressure sensors, which sense the pressure in line W2 and change switching states in response to reaching a predetermined pressure. Each of the switches is coupled to gas supply solenoid S1 to de-energize (close) said solenoid when the respective predetermined pressures are reached.

Connected upstream of pressure control means PS in line W2 is a pressure gauge 22 for monitoring the line pressure, bulk head fitting 24 for connecting line W2 to the test apparatus, and sealing head 26 which couples the water supply system to bottle TB.

A gas system is provided to pressurize the water in line W2 and bottle TB exerting a compressional force on piston 28 to thereby compress the water in chamber 20A of pressure cylinder 20.

The gas system includes a gas supply means in the form of a $CO_2$ cylinder 30 coupled through a supply valve 32 to a gas supply line G1. A $CO_2$ cylinder is chosen, since cylinders of this type are readily available at bottling plants. However, it should be understood that other forms of gas supplies may be utilized without departing from the spirit and scope of the present invention.

Supply line G1 may comprise a flexible rubber tube and may include therein a quick connectors 34, 35, 44. Also included in gas line G1 is a pressure regulator valve 36, a cracking relief valve 38, pressure gauge 40, filter 44, and an adjustable flow and ramp control valve 46. All of the above facilitate the supply of clean $CO_2$ gas of a selected pressure to flow from tank or cylinder 30 to chamber 20B in pressure cylinder 20.

Also coupled to line G1 is a normally closed solenoid valve S1 and a vent line G2 including a normally open solenoid valve S2 and a muffler M. By proper operation of valves S1, S2, chamber 20B can either be supplied with $CO_2$ gas of a predetermined pressure or vented to the atmosphere. The operating sequence of valves S1, S2 is controlled by timer 50 and pressure switches PS, as will be described hereinafter.

Timer 50 for use in the system of FIG. 1 is uniquely designed to embody commercially available components. The timer 50 generates a plurality of electrical pluses of predetermined durations in controlled sequence. A specific example of a preferred embodiment of the timer 50 is illustrated in FIG. 3B to be described hereinafter.

The function of timer 50 is to assist in coordinating switches PS, S1 and S2 in a predetermined sequence to effect automatic operation of a series of tests on bottle TB at discrete and predetermined pressure levels (pass levels).

The initiation of the operation of timer 50 is controlled by control panel 60 which includes ON-OFF switches, safety interlocks, and pressure indicating means which will be more fully described with reference to FIG. 3A.

Figure 2:
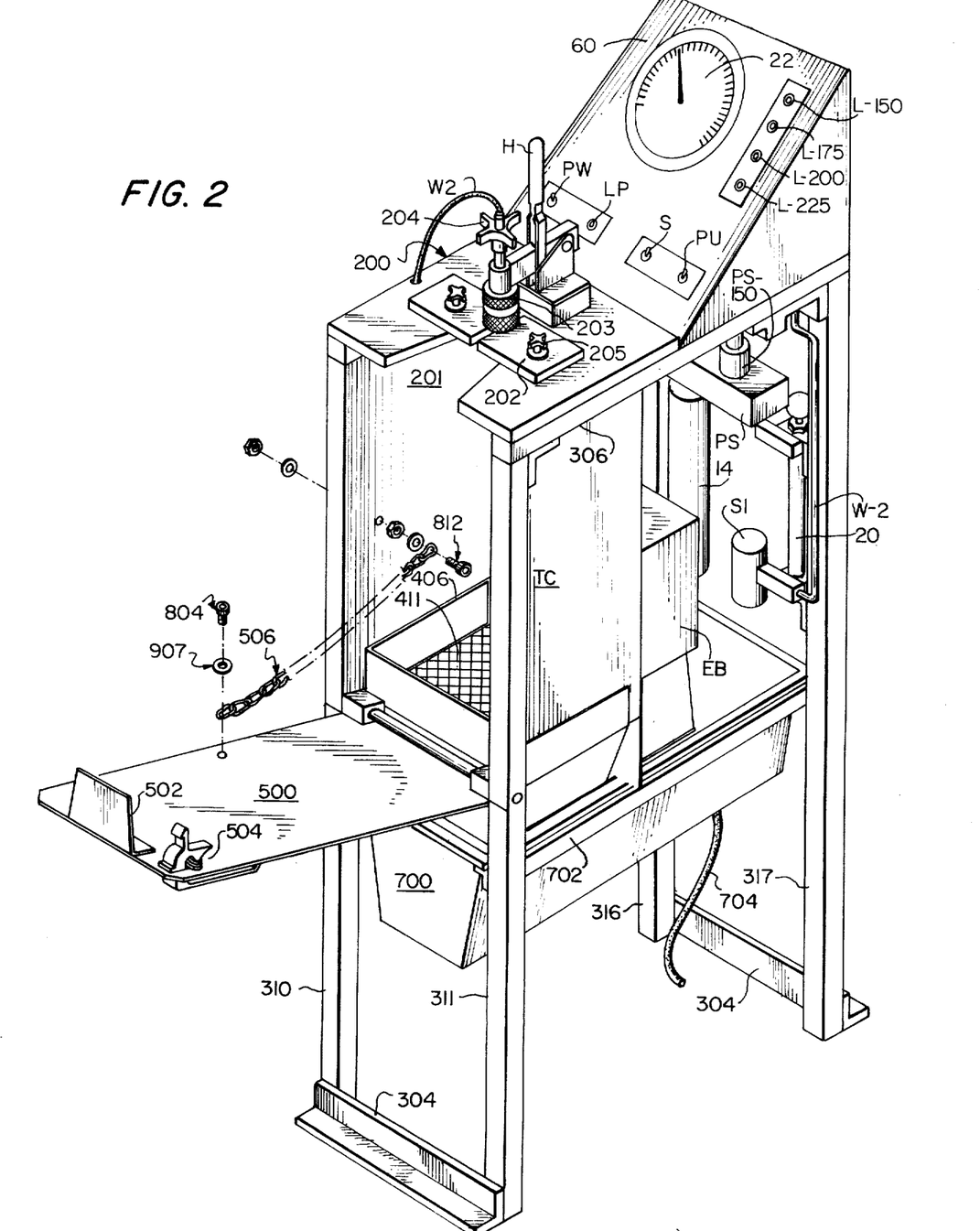
FIG. 2 is a perspective view of the mechanical assembly of the present invention for housing the system of FIG. 1.

Referring to the operation of the test system of FIG. 1 water is supplied to lines W1, W2 where it is permitted to continuously flow, unclamped, through said lines to purge the lines of any foreign matter or gas. The bottle TB is filled with water and then clamped to sealing head 26 to provide a pressure tight seal. A door of the test apparatus to be described with reference to FIG. 2 is then closed which actuates a safety switch enabling the electric system of the present invention. This provides a safety interlock. Then a start button on control panel 60 is pushed which closes vent solenoid S2 and opens solenoid S1 permitting gas to flow into chamber 20B. The pressure of the gas in chamber 20B drives piston 28 upwardly against the water in chamber 20A. Thus, the water is pressurized by the gas or stated another way, the gas pressure is converted to hydrostatic pressure.

As the pressure of water in line W2 and bottle TB begins to rise, there is a visual indication of pressure on gauge 22. The pressure in line W2 is then permitted to rise to a level of 150 p.s.i. and remain at that level for a fixed duration determined by command pulse TD-150. Timer 50 holds the pressure at this level for said fixed duration (i.e. 4 seconds) and then allows the pressure to increase again. This process of stopping and starting the pressure increase in line W2 continues until the desired number of levels (i.e. 150 p.s.i., 175 p.s.i., 200 p.s.i. and 225 p.s.i.) have been reached and held for said fixed duration.

When the last level i.e. 225 p.s.i. has been reached and exists for said fixed duration timer 50 generates control signals which close solenoid S1 and open solenoid S2 to thereby vent gas chamber 20B. Should a bottle TB break during any of the test, indicator means are provided on control panel 60 to light up (i.e. lamps L150, L175, L200, L225) and indicate the test levels passed.

It should be understood that the number and magnitude of test levels discussed above, (i.e. four at 150 to 225 p.s.i.), are offered only by way of example and not by way of limitation. Any number of pressure switches PS can be chosen or adjusted to effect any desired pressure levels or number of levels without departing from the spirit and scope of the present invention.

Referring in detail to FIG. 2 there is illustrated a mechanical assembly for supporting the test bottle of the system of FIG. 1 and portions of the automatic system controls.

As shown in FIG. 2 there is provided an upstanding frame assembly including vertical posts 310, 311, 316, 317. The posts are strengthened at the bottoms by cross braces 304 and at the tops by cross braces 306.

Mounted within the frame structure is a test chamber TC which is closed on three sides in the vertical plane and is provided with an opening through which a test bottle TB is inserted. A door 500 is pivotally mounted within the test chamber opening by suitable hinge means. Door 500 is provided with a spring biased latch 504 and a tongue 502 which mates with slot 201 in the top of test chamber TC. A door supporting chain 506 is secured at one end to door 50 by screw 804 and washer 907 and at the other end to post 310 by nut and bolt combination 812.

Door 500 when closed actuates a safety interlock switch DS as will be described hereinafter with reference to FIGS. 3A to 3C.

A glass catch pan assembly 406 is provided within test chamber TC and includes a bottom 411 in the form of a grate, which permits liquid to flow therethrough if a bottle should break. Tray 406 is removable to facilitate the removal of broken glass therefrom.

Slidably disposed below tray 406 on a pair of tracks 702 is a water drip pan 700 for receiving water passing through grate 411. A suitable drain hose 704 is coupled to the bottom of drip pan 700.

A bottle supporting and sealing assembly 200 is suitably secured to top cross braces 306 and includes bottle head receiving jaws which comprise a pair of plastic pivotable plates 202. Plates 202 pivot about axes passing through screw adjusting means 205. Accordingly, when a bottle is to be introduced between jaws or plates 202, plates 202 are pivoted about the respective axes to open the jaws. The jaws are then closed around the bottle and locked in place by adjusting means 205. Thus the bottle is fully supported by jaws or plates 202.

The test head includes a test head adjusting ring 203 and a test head lock nut 204 which may be brought into sealing engagement by pulling handle H forward. The adjusting ring 203 is utilized to obtain the correct pressure of the seal on the test bottle. Water enters the bottle through water line W2 and the pressure head.

Also mounted on cross braces 306 at the top portion of the assembly of FIG. 2 is a control panel 60. The control panel includes a pressure gauge 22, indicator lights L-150, L-175, L-200, L-225, stop switch S, start switch PU, power switch PW, and power indicator lamp LP. The function of these elements will be discussed hereinafter with reference to FIGS. 3A to 3B.

Pressure control switches PS are mounted just below control panel 60 and extend between cross braces 306. The bottom of switches PS are accessible from the back of the frame assembly to facilitate for adjustment or calibration thereof. Water is supplied to switches PS by water line W2 as explained heretofore in FIG. 1.

Also illustrated within the frame structure of FIG. 2 is $CO_2$ solenoid supply valve S1, pressure cylinder 20, electrical circuit box EB, and inlet water filter 14 which have hereinbefore been described with reference to FIG. 1.

Thus the apparatus of FIG. 2 provides a compact substantially portable test assembly for testing the internal pressure strength of test bottles TB. The assembly includes, when door 500 is closed, a completely enclosed test chamber which precludes injury of the test operator. The safety interlock on door 500 also precludes pressurization of the test bottle before door 500 is closed.

Figure 3A:
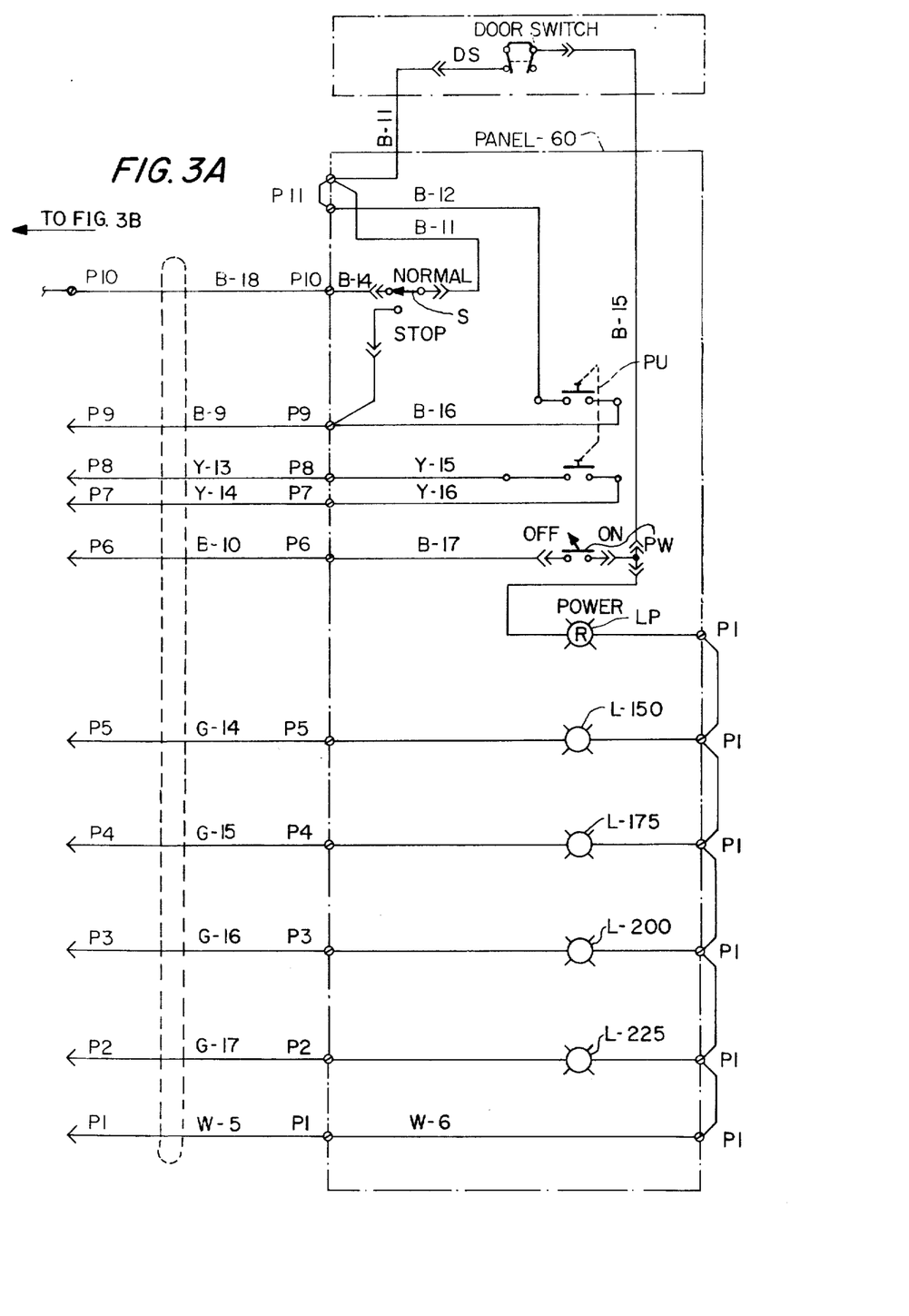
FIGS. 3A to 3C are schematic diagrams of the electrical control circuitry for controlling the testing system of FIG. 1.
Figure 3B:
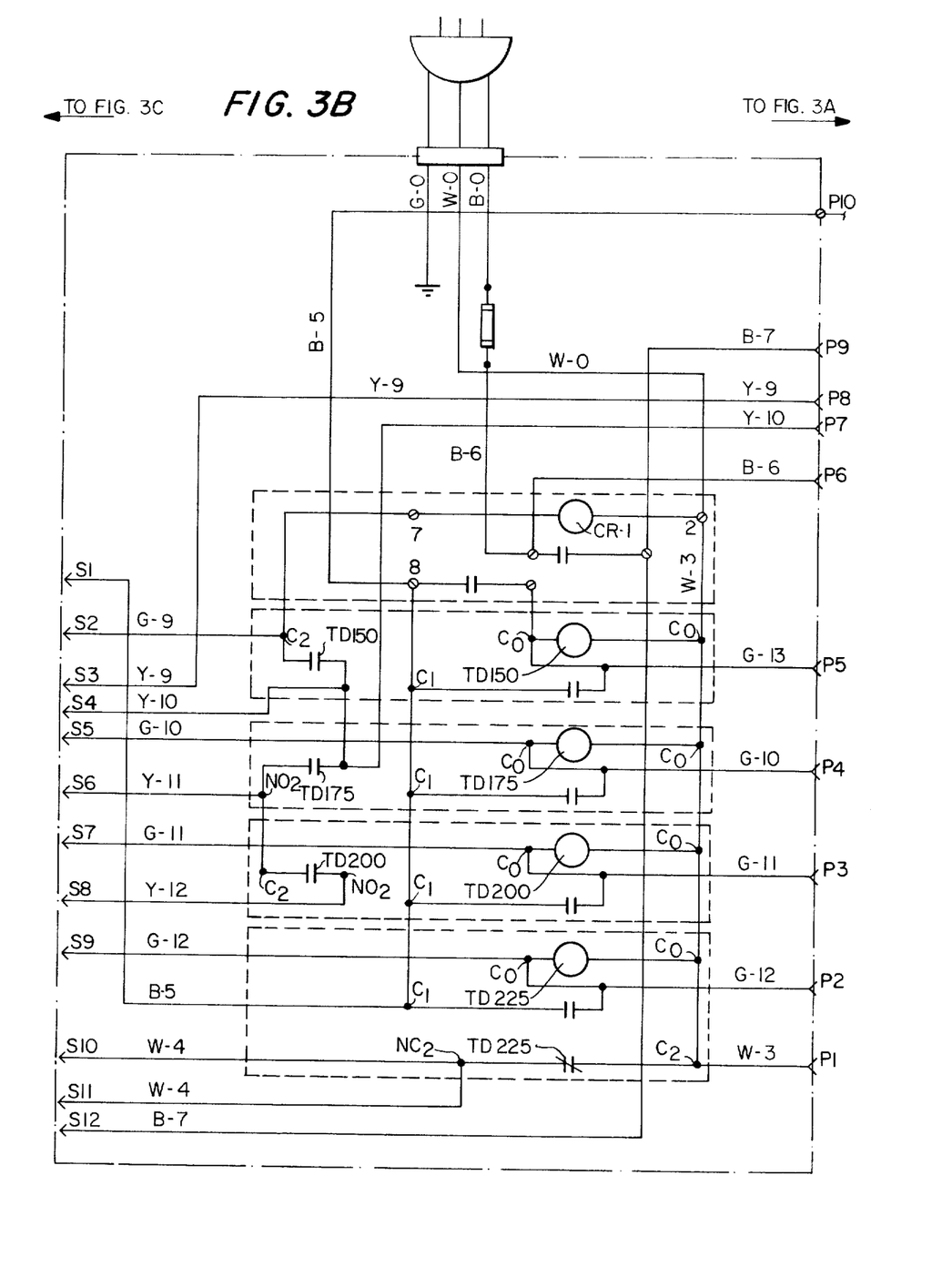
Figure 3C:
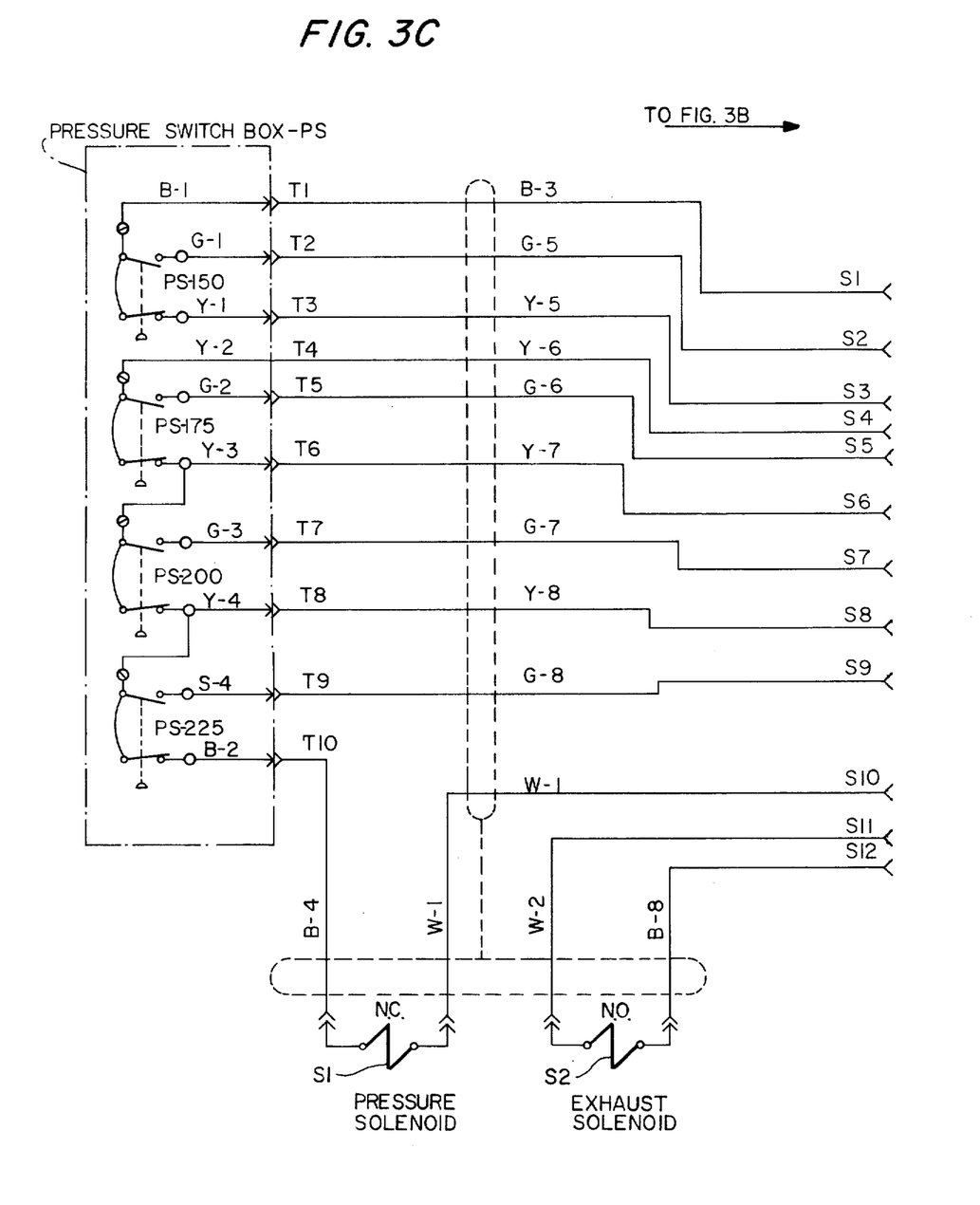

Referring in detail to FIGS. 3A to 3C of the drawings there is illustrated a preferred embodiment of the automatic electronic control circuitry of the present invention. The control circuitry contains four circuit boards or boxes which include the control panel 60 of FIG. 3A, the timer panel 50 of FIG. 3B, and the solenoid and pressure switch panels of FIG. 3C. These panels are all interconnected by snap-type circuit connectors. For example, control panel 60 of FIG. 3A is connected to the right hand side of timer 50 of FIG. 3B by snap connectors P1 to P10. In a similar manner the solenoids S1, S2 of FIG. 3C are connected to the bottom left hand side of timer 50 of FIG. 3B by snap connectors S10 to S12. The pressure switch box PS is connected through snap connectors T1 to T9 to snap connectors S1 to S9 on the left hand side of timer 50 of FIG. 3B.

Referring specifically to the control panel 60 of FIG. 3A there is provided a door switch DS, a stop switch S, a push button start switch PU, and a power switch PW. All of said switches are connected in a safety interlock arrangement to be described hereinafter.

Door switch DS is operatively disposed to open or close the circuit between lines B-11 and B-15. Stop switch S is connected in circuit between lines B-11 and B-18. Push button switch is connected between both lines B-12, B-16 and Y-15 Y-16. Power switch PW opens or closes the circuit between lines B-15, B-17.

Also included in the control panel 60 of FIG. 3A are a plurality of visual indicator lamps including power ON indicator lamp LP and lamps L-150, L-175, L-200, L-225 which correspond to the test pressure levels generated by pressure switches PS of FIG. 3C. Accordingly, when pressure control switch PS-150 has been energized lamp L-150 is energized. Lamps L-175, L-200, and L-225 are energized in turn as the corresponding pressure levels are reached.

The control panel 60 of FIG. 3A is connected to timer 50 of FIG. 3B by snap connectors P1 to P10 via lines W-5, G-17, G-16, G-15, G-14, B-10, Y-14, Y-13, B-9 and B-18, respectively.

Referring specifically to the timer panel 50 of FIG. 3B there is illustrated a three prong plug 461 for connection to a conventional 110–120 volt 60 cycle grounded outlet. A power cord extends from plug 461 to timer housing 50 through retaining means 646. A five amp. fuze may be provided in the hot line B-0 if desired. Timer 50 includes a plurality of relay coils, as indicated in circles CR1, TD150, TD175, TD200, and TD225. The prefix TD refers to time delay and the following number in each instance corresponds to the pressure level switches which they control. Each of the relay coils have corresponding normally open or normally closed contacts, as illustrated, bearing the same nomenclature to assist in the understanding of the operation of the timer circuit. Each of the time delay relay coils and associated contacts are coupled through leads G9, Y9, Y-10, G-10, Y-11, G-11, Y-12, G-12, B5 and W4 to appropriate terminals of corresponding pressure switches PS. As will be explained further hereinafter the relays of timer 50 are energized sequentially in a stepped manner to effect desired pressures of predetermined durations.

Referring specifically to FIG. 3C there is provided a band of four pressure switches PS-150, PS-175, PS-200 and PS-225. The respective switches are connected via lines B-1, G-1, Y-1, Y-2, G-2, Y-3, G-3, Y-4, G-4, B-2, to snap connectors T1 to T10, respectively. Snap connectors T1 to T9 are in turn connected to snap connectors S1 to S9 via lines B-3, G-5, Y-5, Y-6, G-6, Y-7, G-7, Y-8, G-8. A solenoid S1 is provided and connected at one end to snap connector T10 via line B-4 and at its other end to snap connector S10 through line W-1. Solenoid S-2 is connected at one end at snap connector S11 through line W-2 and its other end to snap connector S12 through line B-8.

The pressure switches PS are normally in the positions shown and change states when the corresponding pressure level of each pressure switch is sensed thereby. For example, pressure switch PS normally has a contact connected to line Y-1 but when a pressure of 150 p.s.i. is sensed in the supply line to the test bottle, the contact to line Y-1 opens and the contact to line G-1 closes. When this occurs there is no current path through solenoid S1 and said solenoid is deenergized (closed) cutting off the flow of gas to the pressure chamber. Each of the other pressure switches function in a similar manner when their respective pressures are sensed.

When time delay relay TD-150 times out, normally open contacts TD-150 close providing a current path through solenoid S1 via line B-1, G-1, G-5, G-9, TD-150, Y-10, Y-6, Y-2, PS-175, PS-200, PS-225, B-2 and B-4. Thus solenoid S1 is opened and pressure in the test bottle is again permitted to rise.

The remaining pressure switches and time delay relays in turn function in a similar manner opening and closing solenoid S1 and stepping the pressure levels in progressive stepped increments.

Figures 4A, 4B:
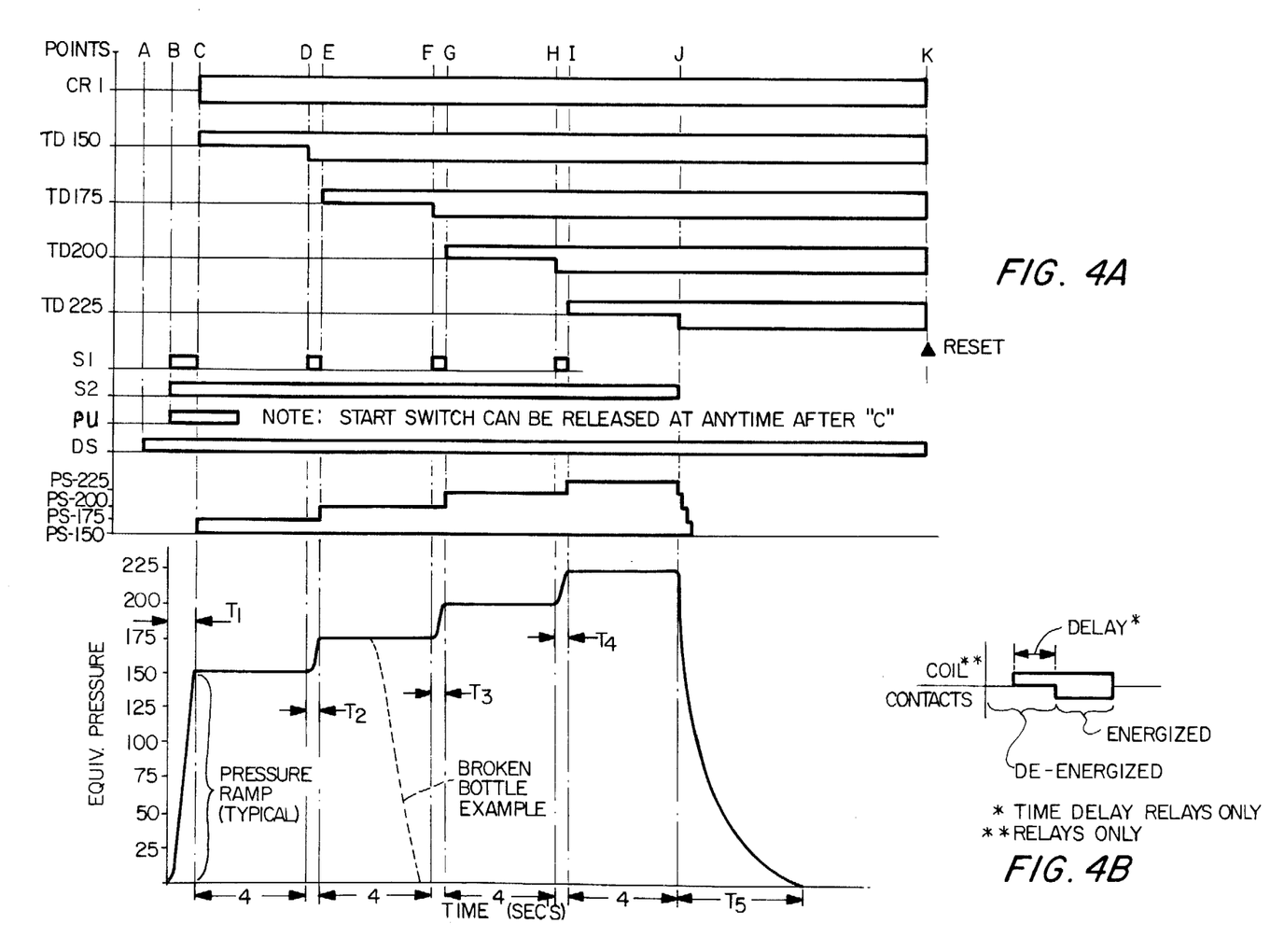
FIGS. 4A and 4B are graphic illustrations of the operation of the circuitry of FIGS. 3A to 3C.

The operation of the control circuit of FIGS. 3A to 3C can be readily understood by reference to the details of FIGS. 4A and 4B.

Referring first to FIG. 4A there is generally illustrated a graphical representation of the operation of the control circuit of the present invention. The abscissa of the graph indicates units of time while the ordinate (upper portion) indicates circuit switching means and the ordinate (lower portion) indicates equivalent pressures. Accordingly, the upper portion of the graph indicates the ON-OFF conditions or status of the circuitry switches with respect to time and the lower portion of the graph indicates the pressure changes in the test bottle with respect to time.

The times T1, T2, T3, T4 and T5, respectively, equal initial ramp time (T1) of the pressure rise in the test bottle, the intermediate ramp times (T2 to T4), and the vent or exhaust time T5.

FIG. 4B is merely a further illustration of the time diagrams of the relays CR1, TD150, TD175, TD200, and TD225 of FIG. 4A. As shown the portion of the timing diagram above the horizontal part line indicates the ON-OFF condition of each relay coil while the portion below said part line indicates the conditions of the corresponding contacts.

The operation of the system and control circuit of the present invention can best be described as sequence of steps A to K displaced in time as indicated along the top of the graph of FIG. 4A. These steps will be described by way of two examples, one under a normal logic sequence in which no bottles break and one a logic sequence in which a broken bottle occurs.

In the following description each step A to K is listed with the occurences at each step indented and listed thereunder.

NORMAL LOGIC SEQUENCE

STEP A. Door shut
   Door switch DS contacts closed
STEP B. Start switch PU activated
   Start switch PU contacts closed.
   Exhaust solenoid S2 energized (closed)
   Pressure solenoid S1 energized (opened)
   Pressure ramp T1 starts
STEP C. Test Pressure reaches 150 p.s.i. equivalent (after $T_1$)
   PS-150 contacts change state
   Pressure solenoid S1 de-energized (closed)
   Pressure ramp T1 stops
   CR1 coil energized — contacts change state in CR1 provides power to the exhaust solenoid after the start button is released. If a bottle breaks the pressure will drop below 150 psi (equivalent) and PS-150 will change state, thereby removing power from CR1. The exhaust solenoid will then be deenergized (vent).
    TD-150 coil energized — beginning time delay
    L-150 lamp is illuminated
    Start Switch PU can be de-actuated
STEP D. TD-150 time delay ends (after 4 seconds)
    TD-150 contacts change state when time delay (TD) relay contacts change state one set of contacts latch or hold the relay and maintain the energized state independent of the original input state. This allows the lamp to remain lit indicating it has passed each sequencial test level(s).
    Pressure solenoid S1 energized (opened)
    Pressure ramp T2 starts
STEP E. Test Pressure reaches 175 p.s.i. equivalent (after T2)
    PS-175 contacts change state
    Pressure solenoid S1 de-energized (closed)
    Pressure ramp stops
    TD-175 coil energized — beginning time delay
    L-175 lamp is illuminated
STEP F. TD-175 time delay ends (after 4 seconds)
    Pressure solenoid S1 energized (opened)
    Pressure ramp T3 starts
STEP G. Pressure reaches 200 p.s.i. equivalent (after T3)
    PS-200 contacts change state
    Pressure solenoid S1 de-energized (closed)
    Pressure T3 ramp stops
    L-200 lamp is illuminated
STEP H. TD-200 time delay ends (after 4 seconds)
    TD-200 contacts change state
    Pressure solenoid S1 energized (opened)
    Pressure ramp T4 starts
STEP I. Pressure reaches 225 p.s.i. equivalent (after T4)
    PS-225 contacts change state
    Pressure solenoid S1 de-energized (closed)
    Pressure ramp T4 stops
    TD-225 coil energized - beginning time delay
    L-225 lamp is illuminated
STEP J. TD-225 time delay ends (after 4 seconds)
    TD-225 contacts change state
    Exhaust solenoid S2 de-energized (opened)
STEP K. Door opened (resets logic)
    Door switch DS contacts open
    CR1 coil de-energized - contacts change state
    TD-150 de-energized - contacts change state
    TD-175 coil de-energized - contacts change state
    TD-200 coil de-energized - contacts change state
    TD-225 coil de-energized - contacts change state
    All lamps return to off state
    Logic reset

BROKEN BOTTLE LOGIC SEQUENCE

STEP A. Door shut
    Door switch DS contacts closed
STEP B. Start switch PU activated
    Start switch PU contacts closed.
    Exhaust solenoid S2 energized (closed)
    Pressure solenoid energized S1 (opened)
    Pressure ramp T1 starts
STEP C. Test Pressure reaches 150 p.s.i. equivalent (after T1)
    PS-150 contacts change state
    Pressure solenoid S1 de-energized (closed)
    Pressure ramp T1 stops
    CR1 coil energized — contacts change state
    TD-150 coil energized — beginning time delay
    L-150 lamp is illuminated
    Start switch PU can be de-actuated
STEP D. TD-150 time delay ends (after 4 seconds)
    TD-150 contacts change state
    Pressure solenoid S1 energized (opened)
    Pressure ramp T2 starts
STEP E. Test Pressure reaches 175 psi equivalent (after T2)
    PS-175 contacts change state
    Pressure solenoid S1 de-energized (closed)
    Pressure ramp T2-stops
    TD-175 coil energized - beginning time delay
    175 lamp is illuminated
LOGIC CHANGE — Bottle breaks after 2 seconds at 175 psi equivalent.
    PS-175 contacts change state
    TD-175 coil de-energized
    L-175 lamp returns to off state
    PS-150 contacts change state
    CR1 coil de-energized - contacts change state
    Exhaust solenoid S2 de-energized (opened)

NOTE

TD-150 contacts do not change state due to latching effect and the 150 lamp remains lit.
STEP K. Door opened (resets logic)
    Door switch contacts open
    TD-150 coil de-energized — contacts change state
    L-150 lamp returns to off state
    LOGIC reset Thus, a completely automatic system for pressure testing a glass bottle through a plurality of discrete and predetermined pressure levels has been described.

It should be understood that the system of the present invention may be modified as would occur to one of ordinary skill in the art without departing from the spirit and scope of the present invention.

What is claimed is:

1. A compact substantially portable system for hydrostatically testing the internal pressure strength of a container automatically at predetermined and adjustable pressure levels comprising:
    means for supplying an aqueous liquid into said container;
    means for pressurizing said aqueous liquid;
    pressure control means for automatically changing the pressure of said aqueous liquid in said container in stepped increments to discrete, predetermined and adjustable pressure levels.

2. The system of claim 1 wherein timer means are provided for controlling the duration of each of said discrete and predetermined pressure levels.

3. The system as defined in claim 2 wherein said timer means generates signals which cause said pressure control means to step said pressure levels from a first level to progressively high levels.

4. The system defined in claim 1 further comprising: indicator means for indicating the value of the discrete predetermined pressure level of a container under test at a given moment in time.

5. The system as defined in claim 4, wherein said indicator means comprises a signal light corresponding to each of said discrete predetermined pressure levels and means are provided for energizing an appropriate one of said signal lights in response to attainment of said discrete predetermined pressure levels in said container.

6. The system as defined in claim 1, wherein said means for pressurizing comprises:
pressure chamber means;
piston means movably disposed within said pressure chamber means,
means coupling said means for supplying aqueous liquid to said pressure chamber on one side of said piston; and
means for supplying gas at a predetermined pressure to said pressure chamber on the other side of said piston;
whereby said gas at said predetermined pressure drives said piston to pressurize said aqueous liquid to a predetermined level.

7. The system as defined in claim 6, wherein said gas is supplied from a $CO_2$ cylinder.

8. The system of claim 6 wherein said means for supplying gas to said pressure chamber includes electrically operable inlet valve means, and said pressure control means includes a pressure sensing switch means for each of said discrete and predetermined pressure levels in circuit with said valve means, said switches sensing each of said pressure levels and changing switching states in response thereto to thereby close said inlet valve means and preclude the flow of gas into said pressure chamber.

9. The system of claim 8 wherein timer means are provided for maintaining each of said pressure levels for predetermined periods of time and opening said inlet valve means at the end of each of said predetermined periods of time to resume the flow of gas into said pressure chamber.

10. The system of claim 1 further comprising:
a test chamber for supporting said container having an access opening therein;
closure means movably supported in said opening for opening or closing said chamber;
electrical power means for energizing said test system; and
safety switch means in circuit with said electrical power means for energizing said system in response to the closing of said closure means.

11. The system of claim 10 wherein there is further provided a removable glass catch tray having a porous bottom and a removable drip pan disposed beneath said porous catch tray.

* * * * *